United States Patent [19]

Maxwell et al.

[11] Patent Number: 4,836,206
[45] Date of Patent: Jun. 6, 1989

[54] METHOD AND DEVICE FOR DETERMINING VIABILITY OF INTACT TEETH

[75] Inventors: G. Maret Maxwell, Wheaton; Richard L. Webber, Myersville, both of Md.

[73] Assignee: The United States of America as represented by the Department of Health and Human Services, Washington, D.C.

[21] Appl. No.: 19,185

[22] Filed: Feb. 25, 1987

[51] Int. Cl.$^4$ .............................................. A61B 5/00
[52] U.S. Cl. .................................. 128/633; 128/664; 128/665
[58] Field of Search ............. 128/632.3, 634, 644–645; 433/29, 25, 32; 356/317, 341

[56] References Cited

U.S. PATENT DOCUMENTS

| | | |
|---|---|---|
| 2,437,916 | 3/1948 | Greenwald . |
| 3,648,685 | 3/1972 | Hepp et al. . |
| 3,674,008 | 7/1972 | Johnson . |
| 3,709,612 | 1/1973 | Clemens . |
| 3,725,658 | 4/1973 | Stanley et al. . |
| 3,811,777 | 5/1974 | Chance . |
| 4,170,987 | 10/1979 | Anselmo et al. ............... 128/665 |
| 4,178,917 | 12/1979 | Shapiro ........................ 128/665 |
| 4,290,433 | 9/1981 | Alfano .......................... 128/665 |
| 4,407,290 | 10/1983 | Wilber .......................... 128/633 |
| 4,479,499 | 10/1984 | Alfano .......................... 128/665 |
| 4,513,751 | 4/1985 | Abe et al. ...................... 128/633 X |
| 4,515,476 | 5/1985 | Ingmar ......................... 128/665 X |
| 4,564,355 | 1/1986 | Traiger et al. .................. 128/633 X |
| 4,575,805 | 3/1986 | Moermann et al. ............. 128/776 X |

Primary Examiner—Kyle L. Howell
Assistant Examiner—Angela D. Sykes
Attorney, Agent, or Firm—Browdy & Neimark

[57] ABSTRACT

An optical technique and device for assessing tooth vitality, involving the use of trans-illumination to detect differentially the relative absence of light absorbed by hemoglobin in circulating blood inside a healthy tooth. White light received from an illuminated healthy tooth is relatively devoid of intensity at a wavelength characteristic of absorption by hemoglobin, when compared with light following the same path in the tooth but of a longer wavelength, by taking the ratio of intensities of the two wavelengths the light of one wavelength is relatively more absorbed by hemoglobin or oxyhemoglobin than the other, indicating the relative amount of blood or oxygen in the blood present in the tooth at the time of the measurement. A broad-spectrum light source is rigidly coupled to a split-beam, differentially-filtered photometer incorporating relatively narrow band filters. Vitality is assessed from the ratio of the scattered light at the two wavelengths, and in change of this ratio overtime.

42 Claims, 8 Drawing Sheets

DEOXYHEMOGLOBIN ABSORPTION SPECTRA

OXYHEMOGLOBIN ABSORPTION SPECTRA

COMBINED ABSORPTION SPECTRA

ABSORPTION SPECTRA OF TOOTH WITHOUT BLOOD

EXPECTED SIGNAL CHANGE FOR NO BLOOD VS. BLOOD

EXPECTED NOISE AS A FUNCTION OF WAVELENGTH

EXPECTED SIGNAL TO NOISE RATIO AS A FUNCTION OF REFERENCE WAVELENGTH

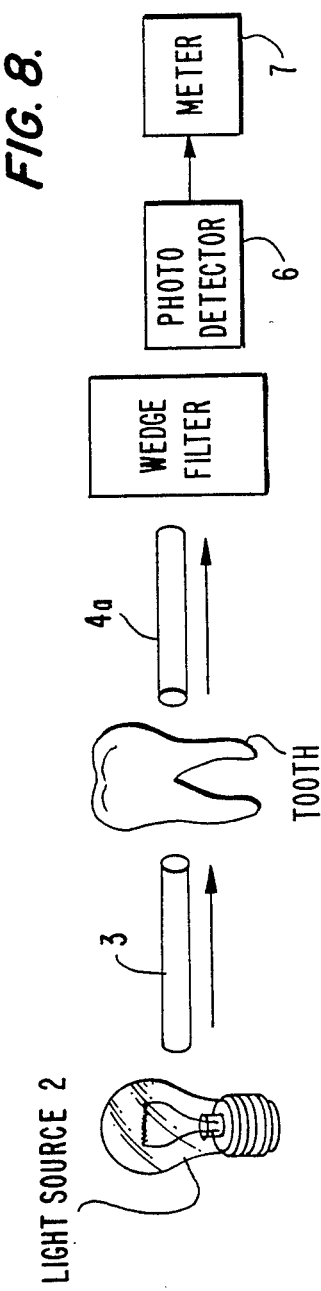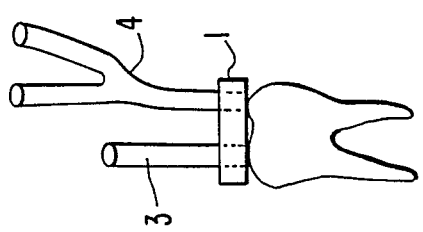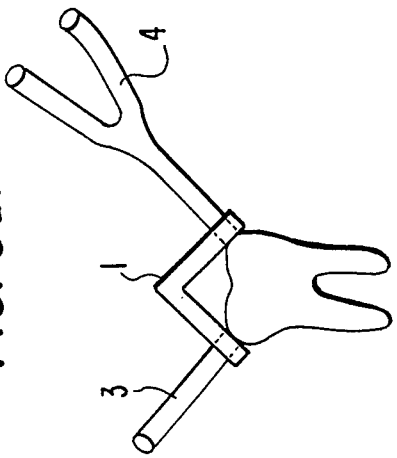

METHOD AND DEVICE FOR DETERMINING VIABILITY OF INTACT TEETH

BACKGROUND OF THE INVENTION

The present invention relates to a method and device for assessing the viability, in other words vitality, of intact teeth, and more particularly to a device and method for assessing the amount of blood in a tooth of a patient based on the ratio of transmission of light of at least two wavelengths.

A well known problem in conventional dentistry is the determination of changes in vitality of a tooth which remains intact in the mouth of a patient. As a patient ages, a tooth can gradually or suddenly lose its circulation of blood, and at some point can essentially become a dead tooth. Although such a dead tooth can continue to function as an intact tooth indefinitely, on the other hand, problems can arise once the tooth loses its vitality and approaches the status of being dead. In any case, it is of interest to the dentist, and certainly to his patient, to be aware of any changes in tooth vitality, even when the change is occurring slowly.

A current clinical method of assessing tooth vitality is to electrically stimulate the tooth, to see if the patient can sense the stimulation. This method has two disadvantages. First, it is limited to the patient's ability to localize the sensation, and second, the presence of irritability does not necessarily indicate that the tooth has intact circulation. Other prior art has involved the use of light for detecting the condition of teeth or for detecting the presence of blood in human tissue. For instance, Alfano in U.S. Pat. No. 4,290,433 (and see also U.S. Pat. No. 4,479,499) teaches a method and apparatus for detecting caries in teeth using the relative luminescence of teeth at two wavelengths. This involves illuminating a surface of a tooth with short wavelength visible light, and collecting the light received back from the surface at longer wavelengths. The spectrum of the received light depends on the extent of the caries or decay which is present on the surface of the tooth. Wilber in U.S. Pat. No. 4,407,290 involves detecting in human tissue a pulse of a varying constituent of flowing blood. Others have sought to measure fluorescence illuminisence in tissue or in the breath of a person (U.S. Pat. Nos. 3,811,777, 3,725,658 and 4,178,917), or to measure optical density in tissue to estimate its dimensions (U.S. Pat. No. 3,648,685, 3,674,008), to map an image of the surface of an object (U.S. Pat. No. 4,564,355, 4,575,805, 4,170,987), or to measure surface color (U.S. Pat. No. 3,709,612, 2,437,916). Prior art efforts in the fields of egg-candeling have addressed the problem of detecting blood in eggs, and pulse oximetry has involved use of different wavelengths for determining relative amounts of oxyhemoglobin and reduced hemoglobin in blood. Photo-plethsmography involves techniques for assessing blood flow. Such prior art is directed to entirely different fields of use and involves determination of different physical properties using different devices and methods as compared to the present invention. None of these prior art techniques involve devices or methods which are available for or suggest assessing viability of intact teeth.

SUMMARY OF THE INVENTION

The present invention is directed to a fixturing device and method for assessing the vitality of intact teeth, based on the presence of hemoglobin in blood therein, as affecting the value of a ratio of intensity of light of at least two wavelengths traversing the tooth. Light in the context used in the present invention is meant to include electromagnetic radiation which need not be limited to the visible spectrum.

The present invention is directed to a device which is easily inserted into the mouth of a patient, to allow for convenient assessing of the viability of his teeth.

The device and method allow predicting whether a single value for the ratio indicates the tooth is viable or not.

The device and method allow establishing a baseline for each tooth of a patient, so that any changes from the baseline that are detected in successive visits by a patient to his dentist can be easily determined.

The device and method are further directed to easily and conveniently allowing a patient and his dentist to monitor the vitality of the patient's teeth.

The invention allows assessing tooth viability by simply forming the ratio of transmitted light of different wavelengths.

BRIEF DESCRIPTION OF THE DRAWINGS

FIG. 8 shows the general concept of a ratiometric system for measuring hemoglobin in intact teeth, wherein a wedge filter is used in determining relative intensities at two or more wavelengths.

FIGS. 9a to 9i show different embodiments of the optical fibers and fixturing device.

DESCRIPTION OF PREFERRED EMBODIMENTS

Figure 1A:
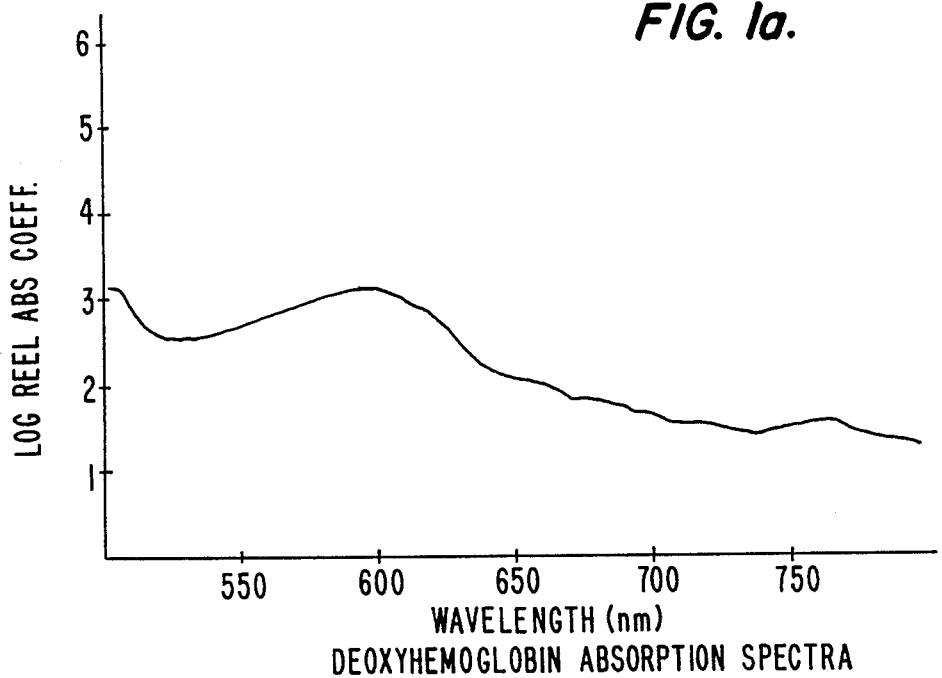
FIG. 1a shows the absorption spectrum of deoxyhemoglobin for the region of 500 nm to 800 nm.
Figure 1B:
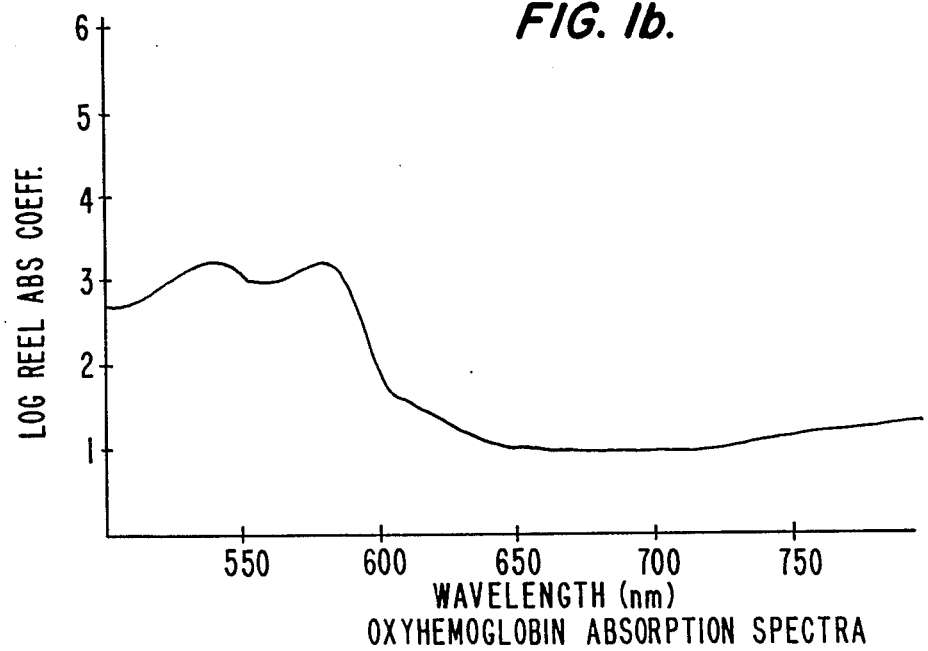
FIG. 1b shows the absorption spectrum of oxyhemoglobin for the region of 500 nm to 800 nm.
Figure 1C:
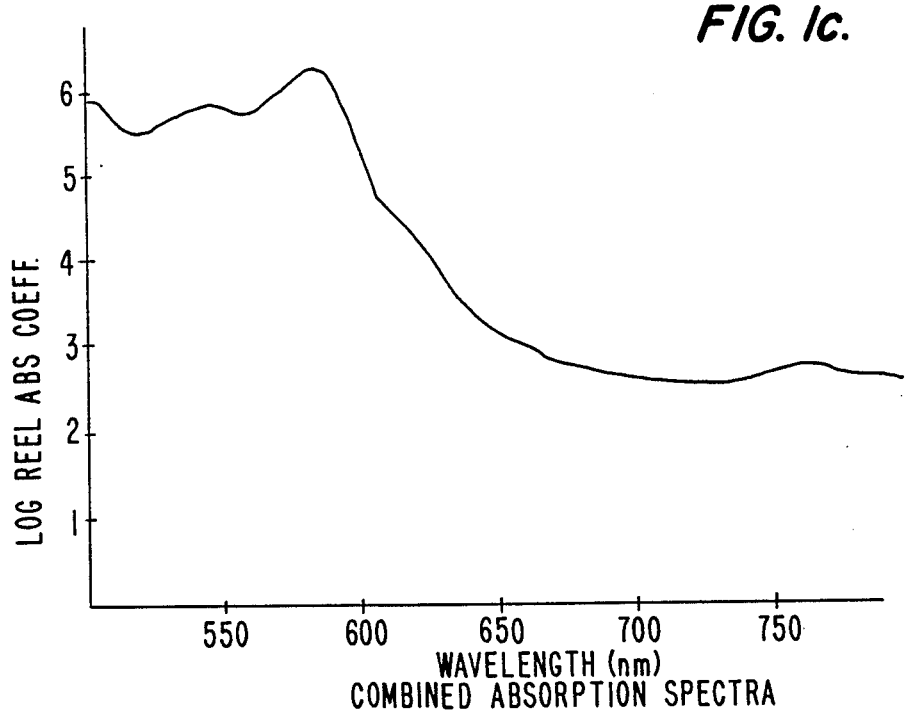
FIG. 1c shows the combined absorption spectra for oxyhemoglobin and deoxyhemoglobin for the region of 500 nm to 800 nm.

The present invention employs the relative transmittance of light through a tooth, for example in the visible and near infra-red, as a result of relative absorption by hemoglobin in blood in the tooth. FIGS. 1a and 1b show the absorption spectra in the visible and near infrared region for deoxyhemoglobin and oxyhemoglobin, respectively. FIG. 1c shows a linear combination of these absorption curves, corresponding to equal amounts of the two types of hemoglobin being present.

The curves are adapted from D. L. Horecker, "The Absorption Spectra of Hemoglobin and its Derivation in the Visible and in Infra-red Regions", J. Biol. Chem, Vol. 48, pp 173–184, 1943. These are the two main constituents of normal circulating blood and are of primary significance for determining tooth vitality according to the present invention.

Figure 2:
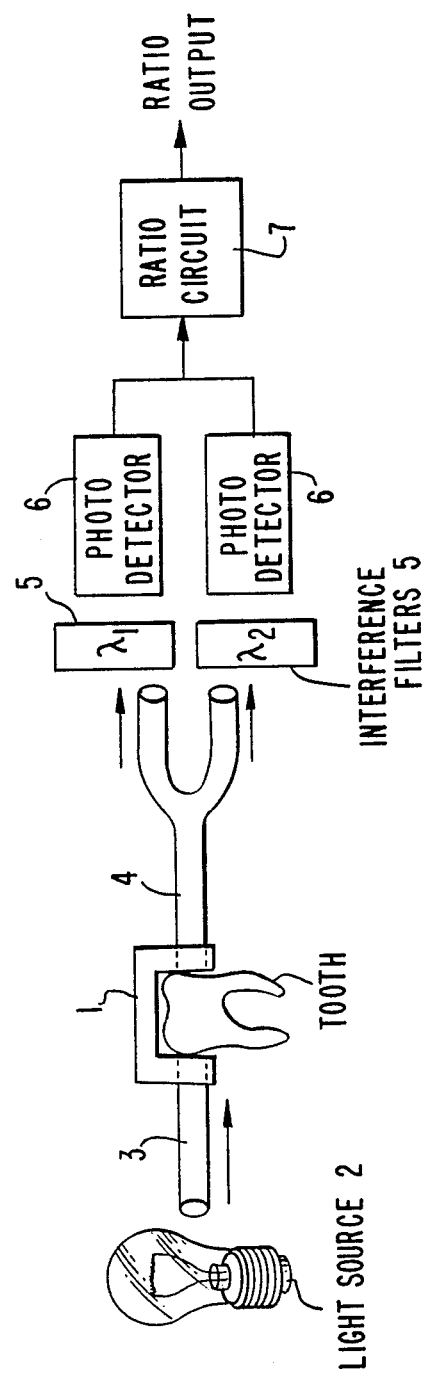
FIG. 2 shows an embodiment of the device of the present invention, including a fixturing device placed around a tooth, and optical fibers and analyzers.

FIG. 2 shows an adjustable fixturing device 1 having portions on both sides of the tooth in the gum of a patient's mouth. This adjustable fixturing device 1 allows light from the light source 2 to be incident via optical fibers 3 onto the tooth. The purpose of this incident light is simply to flood the tooth with the incident light. It is not necessary that the incident light be supplied to the tooth on the opposite side from where the optical fibers 4 receive the light scattered by the tooth. The optical fibers 4 divide to provide separate inputs to respective filters 5. Each filter 5 passes a respective wavelength from the light collected from the tooth, and optical detectors 6 provide outputs corresponding to the amount of light passed by each filter. The ratio circuit 7 electronically divides one signal into the other, and outputs a signal indicating the ratio of the intensities of the received light at the two wavelengths. A broad band source can be used for the light source 2, without excessive concern for its stability, in view of the ratio of the two wavelengths from the light source that is measured as a result of the filters 5, optical detector 6 and the electronic divider 7. Collimators, not shown in FIG. 2, can be provided before the filters 5.

FIG. 1c shows a pronounced absorption peak for the combined spectra at a wavelength of approximately 585 nm. The amount of absorption in this vicinity of wavelength will depend particularly upon the presence of hemoglobin in the pulp of the tooth.

Figure 3:
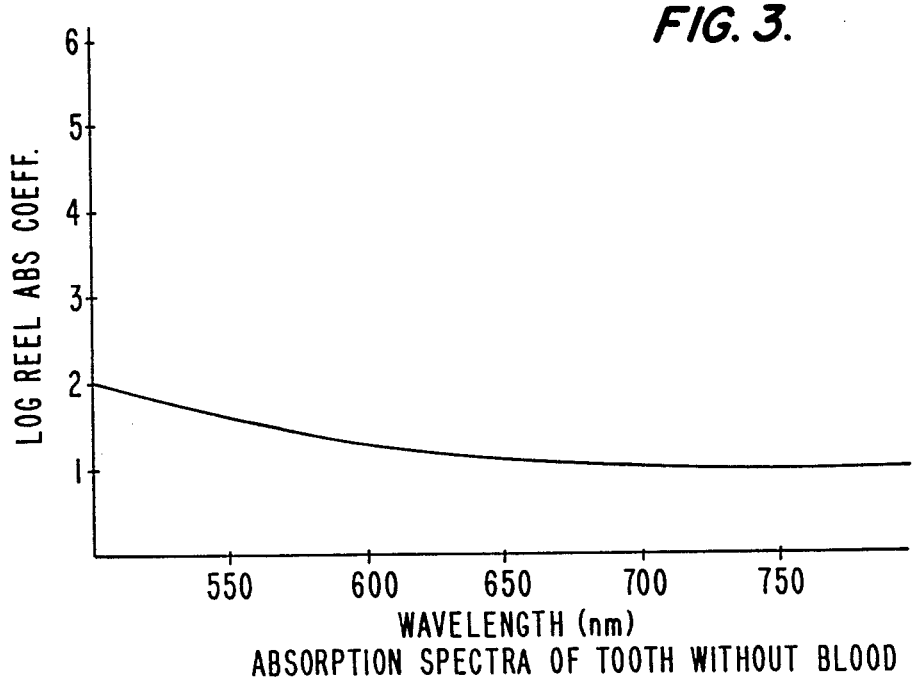
FIG. 3 shows the absorption spectra of a tooth which is devoid of hemoglobin for the region of 500 nm to 800 nm.

FIG. 3 shows the absorption spectra of a tooth which contains no blood. White light passing through a tooth which contains blood will be absorbed in a manner determined by a combination of the absorption spectra such as of FIGS. 1c and 3. White light passing through a tooth which contains no blood will be absorbed in a manner determined only be the absorption spectrum of FIG. 3. Thus the ratio of light at two wavelengths will be different for a tooth containing blood and a tooth without blood. The percentage change of the ratio of a tooth with blood to a tooth with no blood will be the expected signal for any given ratio of wavelengths.

Figure 4:
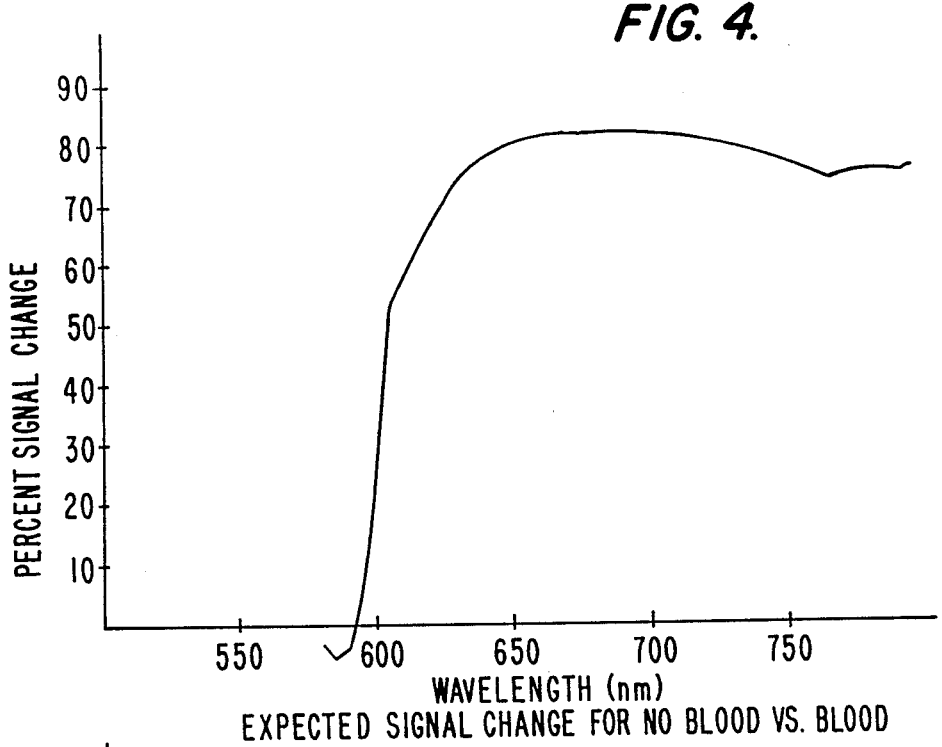
FIG. 4 shows the expected percentage change in signal for a tooth which goes from havingnormal circulation to having to hemoglobin when the ratio measured is for 575 nm to wavelengths from 580 nm to 800 nm.

FIG. 4 shows the expected signal change when the first wavelength is selected at 575 nm and the second wavelength varies from 580 nm to 800 nm. This expected signal change is based on a linear combination of the absorption spectra of FIGS. 1c and 3. Further study may reveal that a linear combination of these two spectra is not the best method for representing the absorption behavior of the tooth. While this will result in a change in the shape of FIG. 4, the method for selecting optimal wavelengths described herein will still be valid.

The path which the light takes in a tooth depends in part upon the wavelength of the light, since some optical properties of the tooth are a function of wavelength. As the difference between the two wavelengths increases, any error caused by changes in path length resulting from changes in the probe position from measurement to measurement can be generally expected to increase.

A test was conducted in which white light emitter from the light source 2 was conducted along an optical fiber 3 to the tooth. The incident white light entered the tooth, where some wavelengths of light were absorbed more than others. Light output from the tooth was collected and connected along the second set of optical fibers 4 to the pair of filters 5, one of which passed light in the vicinity of 575 nm and the other passed light of either 585 nm, or 795 nm. Fixturing device 1 was not employed, so that measurements could be made with the fibers 3 and 4 placed in arbitrary geometrical relationships. A series of ten measurements were made for each of three teeth at each of three wavelengths (585 nm, 655 nm, 795 nm). The results of these measurements are given in Table A.

TABLE A

Experimental determination of the statistical variability of measured intensity ratios as a function of wavelength of the tooth viability detector.

| | Wavelength Ratio | | | | | | | | |
| --- | --- | --- | --- | --- | --- | --- | --- | --- | --- |
| | 575/585 nm | | | 575/655 nm | | | 575/795 nm | | |
| | M | S | N | M | S | N | M | S | N |
| Tooth 1 | 1.018 | .053 | 5% | .470 | .049 | 10% | .508 | .114A | 22% |
| Tooth 2 | .983 | .062 | 6% | .412 | .063 | 15% | .402 | .120 | 30% |
| Tooth 3 | .949 | .067 | 7% | .428 | .066 | 15% | .366 | .103 | 28% |

M - Mean of measurements
S - standard deviation of measurements
N - S/M × 100 percent variation or noise The ratio of the standard deviation to the mean expressed as a percentage is taken to be the noise. A curve was fitted to the data of Table A and is shown as FIG. 5. wherein the noise is shown as a function of the second wavelength employed.

The best embodiment of this device will be one in which the signal-to-noise ratio is maximized. The signal-to-noise ratio may be improved by either decreasing the noise or by increasing the signal. A variety of ways can be utilized to achieve such improvement. FIG. 6 shows the signal to noise ratio as a function of wavelength as determined from FIGS. 4 and 5. From this an optimal second wavelength to be used with a first wavelength of 575 nm may be determined. In this case an optimal wavelength is seen to be in the vicinity of 625 nm. A series of curves similar to that of FIG. 6 may be created for any set of wavelengths, so that two optimum wavelengths to be employed may be selected.

A further test was conducted, in which white light emitted from the light source 2 was conducted along an optical fiber 3 to the tooth. The incident white light entered the tooth, where some wavelengths of light were absorbed more than others. Light output from the tooth was collected and conducted along the second set of optical fibers 4 to the pair of filters 5, one of which passed light in the vicinity of 575 nm and the other passed light of 795 nm. Fixturing device 1 was employed so that measurements could be made with the fibers 3 and 4 placed at the same anatomical points on the tooth each time. In this test the noise was found to average 16%, whereas in the test whose results are given in Table A the average noise for these two wavelengths was 27%. Thus it was demonstrated that the use of fixturing device 1 can substantially reduce the noise of the measurements.

Figure 5:
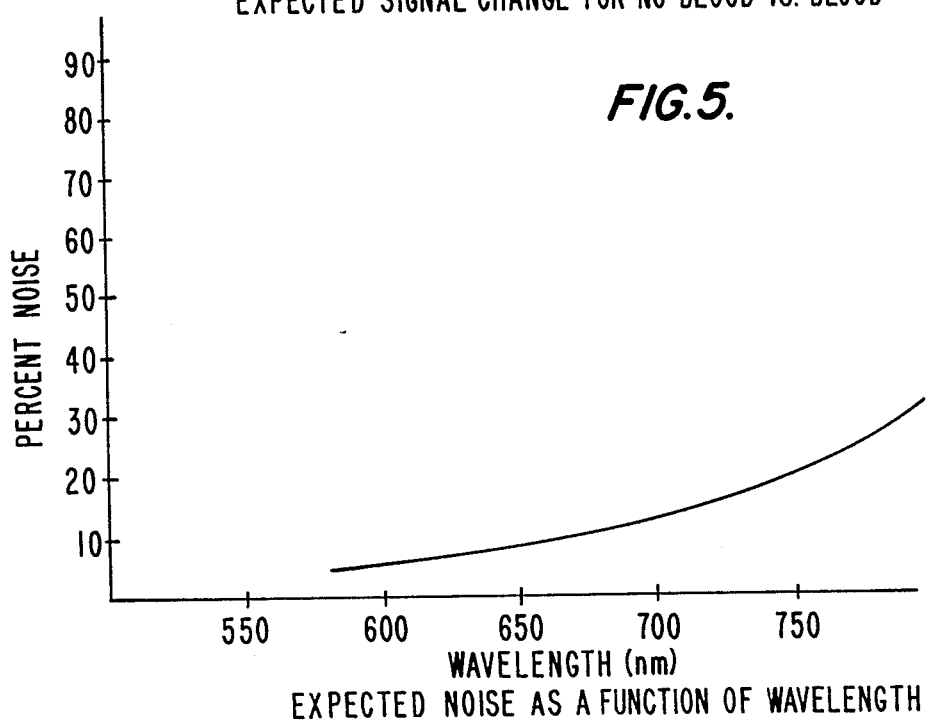
FIG. 5 shows the expected percentage noise of the measurements as a function of wavelength from 580 nm to 800 nm.
Figure 6:
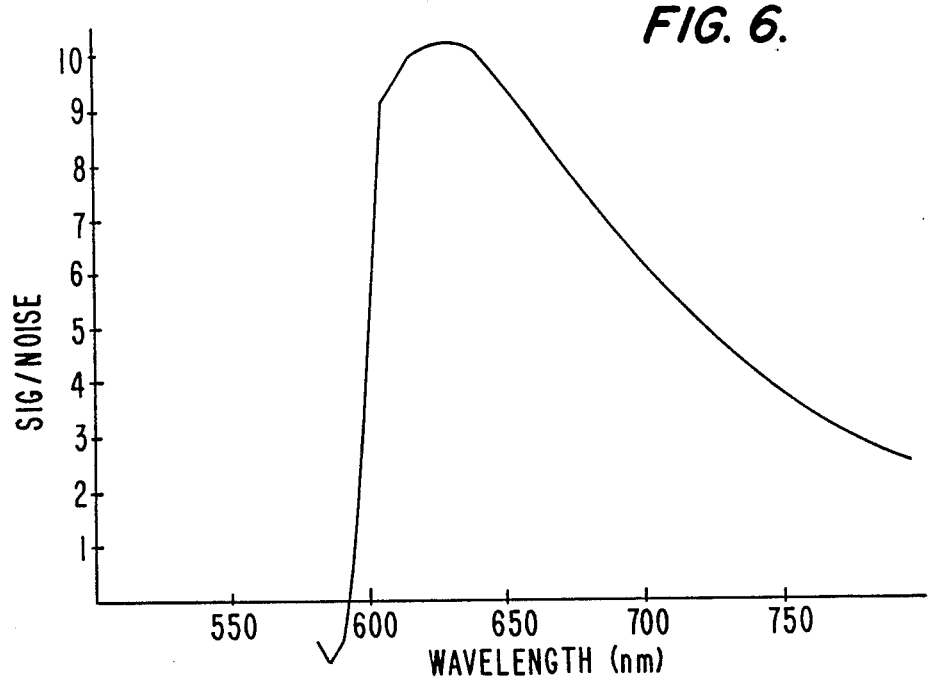
FIG. 6 shows the expected signal-to-noise ratio as a function of wavelength when the first wavelength is selected at 575 nm.

FIGS. 4 and 5 represent only the present understanding of light absorption by the tooth. Further study may reveal that curves of different shapes may better represent the nature of the signal and noise. In any case, the maximum ratio of signal to noise will still determine the optimal selection of wavelengths, as demonstrated by FIG. 6.

A further test was conducted, using 595 nm as the second wavelength. White light emitted from the light source 2 was conducted along an optical fiber 3 to be fixturing device 1. The incident white light entered the tooth, where some wavelengths of light were absorbed more than others. Light output from the tooth was collected and conducted along the second set of optical fibers 4 to the pair of filters 5, one of which passed the light with wavelength in the vicinity of 585 nm and the other passed light in the vicinity of 595 nm. The absorption by the tooth of the light near the second wavelength, namely at 595 nm, was less, as a result of absorbing a smaller part thereof. Thus, use of the ratio of the first and second wavelengths is to compensate for the total amount of light passing through the tooth which will change with the intensity of the light and the path of the light through the tooth.

The ratio of intensities of the light at the two wavelengths is a measure of the amount of hemoglobin in the tooth. The value of the ratio of the intensity of the 595 nm light to the 585 nm light is expected to decrease as the amount of hemoglobin in the tooth decreases. This trend was observed experimentally with extracted teeth, the results of the experiment being given in Table B in terms of the inverse of this ratio, namely the 595/585 less absorbtion ratio of the intensity of the 585 nm light to that of the 595 nm light. This shows the ratios of the intensities for these two wavelengths, readings #1 indicating observations on a freshly extracted tooth, and readings #2 and #3 having been made at later times after the hemoglobin had broken down.

TABLE B

Experimental ratios of tooth viability detector.

| | Reading # | | |
|---|---|---|---|
| | #1 (8-29-85) | #2 (9-10-85) | #3 (9-24-85) |
| Tooth one | 0.88 | 0.81 | 0.83 |
| Tooth two | 0.94 | 0.85 | 0.87 |
| Tooth Three | 0.98 | 0.87 | 0.86 |

The percent change between a tooth with no blood is about 10% as determined by the results of Table B. The noise at these two wavelengths is about 5% as determined by FIG. 5. The signal-to-noise ratio for these two wavelengths would thus be about 2 as is predicted by FIG. 6.

Figure 7:
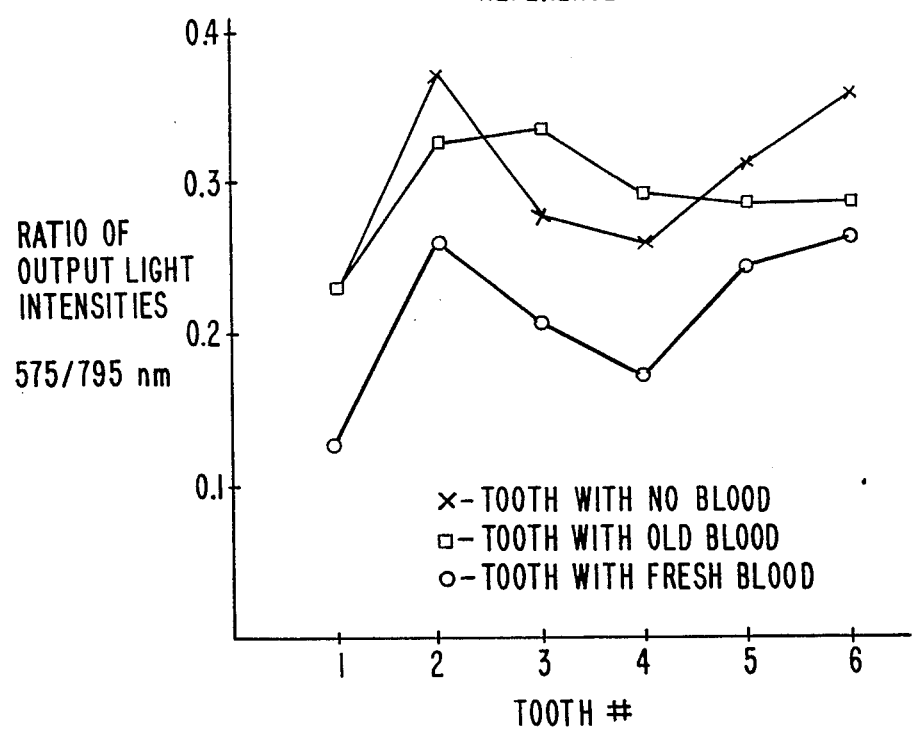
FIG. 7 shows the resulting change in the measured wavelength ratio for six teeth as they go from a state of normal blood content to a state of no blood.

Tests were conducted using this second set of wavelengths on extracted teeth which initially did not contain any blood. Subsequently each tooth was injected with a quantity of blood representative of that which would be found in a healthy intact tooth, and the measurements were repeated. Each measurement consisted of determining the transmitted light ratio 5 times in each of two positions for a total of 10 measurements, for each of 6 teeth. After each tooth was injected with blood, an identical set of measurements was then made, during the time that the injected blood was considered as fresh blood. Following this further set of measurements, the teeth and a sample of the blood were refrigerated, and the blood sample was checked with a spectro-photometer periodically over a period of two weeks, until it was clear that the hemoglobin had broken down into other components not having such absorption. A final set of measurements was then performed. The results are shown in FIG. 7, wherein it is clearly seen that the ratio of the 575 to the 795 nm light decreased with the presence of fresh blood as expected. An analysis indicates that these differences are statistically significant, at a level well above the 99% confidence level. The percent change between a tooth with blood and a tooth with no blood is about 80% as determined by the results of FIG. 7 and predicted by FIG. 4. The noise at these two wavelengths is about 28% as determined by FIG. 5. The signal-to-noise ratio for these two wavelengths would thus be about 2.8, consistent with a prediction based on FIG. 6.

These findings above support the general usefulness of the present invention for assessment of tooth vitality, and further as a means of quantifying change in the circulation of a given tooth over time.

There is a second factor which affects the amount of light absorbed by a tooth. This is the distance the light must travel wighin the tooth, namely from the point where the incident light is provided to where the scattered light is collected from the ratio wavelengths. In the embodiment illustrated in FIG. 2, the fiber optic bundles 3 and 4, as a result of having the relative position of their ends rigidly fixed in the fixturing device 1, deliver and collect the light at well defined points with respect to each other. Thus, the measurements can be repeated on any given tooth with acceptable experimental error, and differences in the value of the ratio between different teeth can be minimized.

A third embodiment of the present invention involves combining in the device and method a third wavelength, for instance at 660 nm. At this wavelength the absorption of oxyhemoglobin is different from the absorption of deoxyhemoglobin. Thus, the ratio of this wavelength to for instance 585 nm can also be formed, in addition to a ratio as above. Forming such a combination of ratios makes possible assessment of the relative amount of oxyhemoglobin present within an intact tooth, by discriminating between the oxyhemoglobin and the reduced deoxyhemoglobin.

The fixturing device can be provided with calibrated adjustment means for locating it in a repeatable fixed position with respect to a tooth. Thus the incident input light and the output light can be repeatedly caused to enter and exit each tooth at the same positions on the surface of the tooth, and along the same direction through a tooth, on successive visits. However, the usefulness of the present invention is not limited in this regard.

The data presented in FIG. 7 show a variability of about 20% for measurements taken on different teeth, whereas the variability expected as shown in FIG. 5 is about 23%. Thus optimal selection of wavelength by the method taught herein as shown in FIG. 6 can result in a device which can assess the viability of a tooth based on a single measurement.

Alternatively, a single wedge filter could be used. The wavelength of light passed by a wedge filter depends upon the point at which light is incident upon the filter and this position could be varied by moving the filter. In this case a single light pipe 4a for the output light is sufficient. This is in fact how the test was performed in which light was measured at 585 nm and 595 nm. A two filter design was considered faster and less sensitive to positioning of the fibers, but there are other ways to overcome these problems which would make a single wedge filter desirable.

Figure 9D:
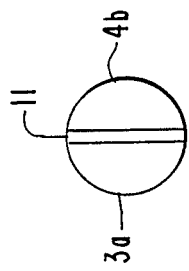
Figure 9C:
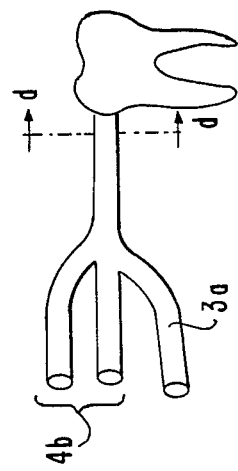
Figure 9F:
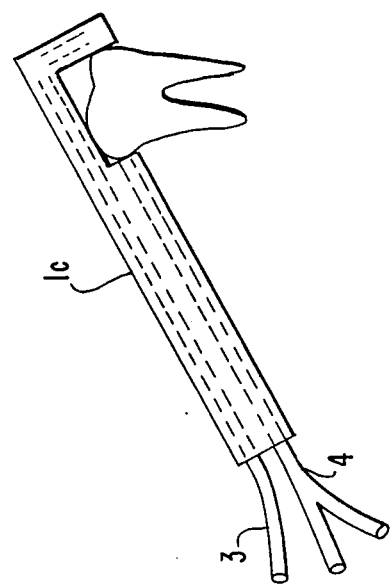
Figure 9E:
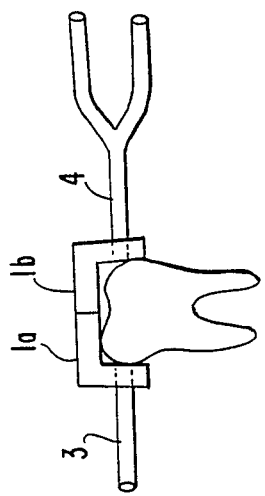
Figure 9G:
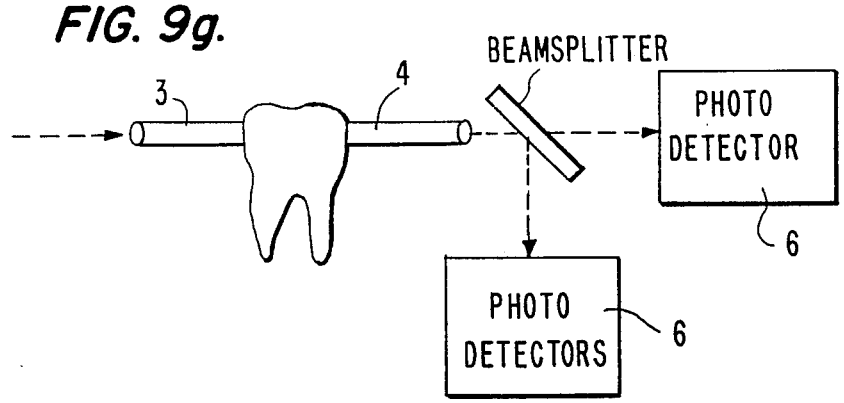
Figure 9H:
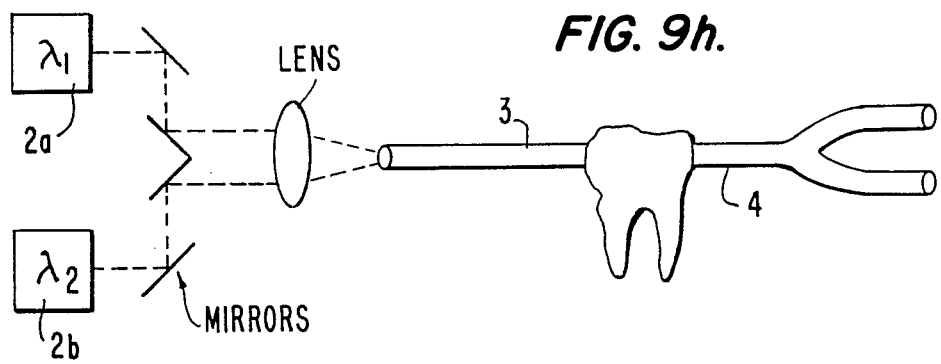
Figure 9I:
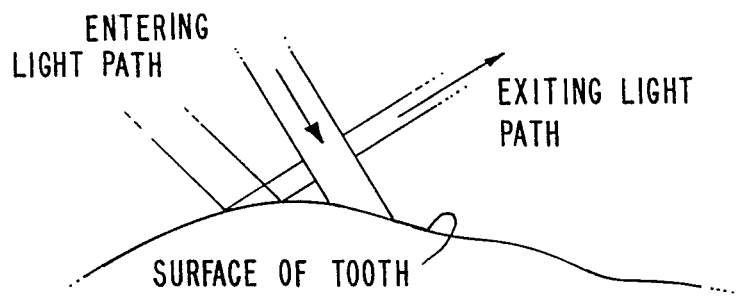

A variety of modifications of the fixturing device and optical fiber bundle is also possible. FIG. 9a shows an angled fixturing device for arbitrary geometry of the input and output light fibers. FIG. 9b shows a fixturing device wherein the input and output light fibers are parallel and brought to nearly the same point in a surface of the tooth. FIG. 9c shows a side view of another embodiment, wherein the input optical fiber 3a is combined with the output optical fibers 4b in the vicinity of the tooth. FIG. 9d shows a cross-section of the combined optical fibers 3a and 4b of FIG. 9c where they contact the tooth, wherein an optically opaque divider 11 separates the two respective bundles. The divider 11 can advantageously be provided of a flexible material, to lie against the surface of the tooth to prevent undesired crosstalk of light between the input and output bundles. Alternatively the entrance and exit angles of the light may be arranged so as to prevent direct reflection of the incident light to the detector as shown in FIG. 9i.

When the data was collected using a fixturing device, it was seen as above that the noise decreases. Thus the primary advantage of a fixturing device is to decrease the noise of the measurements and hence increase the signal to noise ratio. There are many ways in which a fixture can be implemented. It can be spring-loaded so as to grab the tooth on two particular surfaces, i.e. the front and back. FIG. 9e shows such embodiment of the fixturing device, which is divided into two parts 1a and 1b connected by an internal spring (not shown) so as to grasp the tooth to hold the fixturing device on the tooth or, it can be shaped like an arc and hooked over the tooth. FIG. 9f shows another embodiment of the fixturing device 1c of a hooking type, with internal fibers. Also, the fibers could be brought to the same side of the tooth, provided direct reflection is prevented, or the fibers could be provided at any desired geometry with respect to each other. Further technical advances or a more specialized design may permit the light source and detectors to be incorporated in the fixturing device.

A bifurcated fiber can be employed to divide the light to the two filters. This could be done with a single fiber which delivered the light to a beam splitter in front of the filters. FIG. 9g shows such an embodiment wherein a bifurcated fiber 4 is replaced with a single fiber and a beam splitter.

Another possibility for improving the noise in the device would be to use monochromatic light sources, such as lasers, for a light source which only contains the two wavelengths of interest. The light exiting the tooth might still have to be filtered, an improvement is to be expected since filters pass light in the vicinity of a given wavelength and not at a single wavelength. While such an approach might be relatively expensive at present, this might change with further technical advances. FIG. 9h shows such an embodiment wherein two monochromatic light sources 2a, 2b of different wavelengths are used with mirrors and a lens to provide the light to the input light pipe 3.

Other arrangements and modifications would be obvious to a skilled worker in the art in possession of the present disclosure. For instance, if imaging is provided for picking up the output light and for controlling the area of input of the input light is incident, then the optical fibers may not need to be in particularly close proximity to the tooth.

Also, it can be seen from the given results that the noise for repeated measurements of the same tooth and measurements of different teeth are of about the same order. This indicates that, if optimal wavelengths are selected as per the method described above, it should be possible to determine the vitality or viability of a tooth based on a single measurement. Thus the device need not be used solely to follow the progression of a tooth with time, but could be used with a single measurement to indicate the current state of a tooth. This is very significant for clinical use of the device of the present invention.

We claim:

1. A device for testing the viability of a patient's teeth, comprising
   mouth insertion means for being inserted into the mouth of the patient, for introducing into each selected tooth light of at least two different wavelengths and for receiving respective output light scattered from within said tooth of said at least two different wavelengths,
   means for determining a value indicating the relative amounts of the received output light of said at least two different wavelengths,
   said mouth insertion means including fixation means for being successively located in the vicinity of each of a plurality of selected teeth of the patient the viability of which is to be assessed, said fixation means including a first respective part from which said light is introduced into each respective selected tooth and a second respective part for receiving the respective output light scattered from within said tooth,
   an external source for said input light,
   a flexible input pipe connected at a first end to said first respective part of said fixation means and to said external source, so that said input light is introduced from said first respective part into each respective selected tooth in the vicinity of which said fixation means is successively located for assessing the tooth,
   a flexible output light pipe connected at a first end to said second respective part of said fixation means for receiving said output light scattered from within the respective tooth, and
   said means for determining including a ratio circuit providing an output corresponding to a ratio of the amounts of light at said two different wavelengths in said output light scattered by each said selected tooth and received by said flexible output light pipe,
   wherein said first and second parts of said mouth insertion means with said ends of said flexible input and output light pipes are provided so that said received output light essentially excludes any light from said first end of said flexible input light pipe and not scattered from within the tooth.

2. The device of claim 1, comprising
   said output light pipe dividing to provide two second ends thereof from which exit two respective parts of said received output light with essentially identical wavelength distributions, and said means for determining including respective light detectors for said two different wavelengths, each said light detector being located to receive the respective part of said received output light exiting from a respective one of said second ends of said output light pipe.

3. The device of claim 2, comprising
said external source of said input light being a source of broad-band light, said broad-band extending to include said two different wavelengths, and
said means for determining including two band-pass filters respectively centered at said two different wavelengths, each located between the respective second end of the output light pipe and the respective light detector.

4. The device of claim 3, wherein
said two different wavelengths for the determining of said ratio for each selected tooth are provided by said external light source and said respective filters to comprise separate bands in the vicinity of 585 and 595 nm, respectively,
said ratio is a predetermined one of the intensity of the band at 595 nm to the intensity of the band at 585 nm or its inverse, and said ratio decreases or increases, respectively, as the amount of hemoglobin in each said selected tooth increases, said viability increasing with increase in the latter of said ratios, and conversely as to the former of said ratios.

5. The device of claim 3, wherein said two different wavelengths are respectively selected by filters to comprise two separate bands, a first of said bands being in a first wavelength region of strong absorption by hemoglobin and the second of said bands being in a second wavelength region where hemoglobin is substantially less strongly absorbing.

6. The device of claim 5, wherein a first of said two different wavelengths is selected at a peak in the absorption of oxyhemoglobin in the vicinity of 575 nm, and the second of said wavelengths is selected in the infra-red where oxyhemoglobin and deoxyhemoglobin are less absorbing.

7. The device of claim 2, comprising
said output light pipe having a further second end from which exits a further part of said received output light having a similar wavelength distribution as said other parts of said received output light,
a further light detector and filter receiving said further part of said received output light from said further second end of said output light pipe, said further filter being centered on a third wavelength different from said two other different wavelengths,
said determining means including means for receiving an output of said further light detector and for providing a further output corresponding to a further ratio, namely of said output of said further light detector with respect to the output of one of said other two light detectors,
wherein said wavelengths are selected for discriminating by said two ratios the relative amounts of oxyhemoglobin and deoxyhemoglobin.

8. The device of claim 7, wherein said further filter is selected to pass a narrow band in the near infra-red.

9. The device of claim 8, wherein said third wavelength passed by said further filter is centered in the vicinity of 660 nm.

10. The device of claim 9, wherein said first and second wavelengths are selected by the respective filters to be in the vicinity of 575 and 795 nm.

11. The device of claim 1, wherein said first and second respective parts of said fixation means from which said input light is provided to each said tooth and from which said output light is received by the output light pipe, respectively, are provided to be on opposite sides of the respective tooth when said fixation means is located over the tooth.

12. The device of claim 1, wherein said first and second respective parts of said fixation means from which said input light is provided to each said selected tooth and at which the output light received from the tooth, respectively, are on the same side of the tooth, when said fixation means is located on each respective tooth to assess its viability, and wherein said input light is prevented from being reflected from a surface of said tooth and being collected with said output light.

13. The device of claim 11, said determining means including a wedge filter which is movable for passing said two wavelengths as said input light at respective different times for respective different positions of said wedge filter for each said tooth to be assessed, and a photodetector for measuring the intensities of said two wavelengths at said respective different times as passed by said wedge filter for each said tooth to be assessed.

14. A method for assessing the viability of teeth of a patient, comprising
flooding each selected tooth of the patient at least successively with broad band input light,
collecting from the vicinity of each respective selected tooth output light emitted from within the respective selected tooth,
dividing said collected output light into two parts having the same wavelength distributions at least in a relative sense within each said wavelength distribution, and
determining a number corresponding to a ratio of intensity in two separated wavelength intervals in respective ones of said two parts of said output light, including taking into account at least the relative amplitudes of said two wavelength distributions,
wherein a first of said wavelength intervals is selected at a wavelength where hemoglobin is highly absorptive, and the second of said wavelength intervals is selected where hemoglobin is substantially less absorptive,
wherein said ratio is indicative of the amount of blood in each respective selected tooth and accordingly the viability of the tooth.

15. The method of claim 14, comprising determining in a first visit a first value for said number corresponding to the ratio for each said selected tooth of the patient,
determining in a subsequent visit a subsequent value for said number for each of said selected tooth, and
comparing said values for said number from said first and subsequent visits for each said selected tooth,
wherein any change between the visits in the viability of each said selected tooth is determined by a comparison of the respective values of said numbers for different visits for each said selected tooth.

16. The method of claim 15, wherein each said selected tooth is flooded with said input light at the same area in said first and subsequent visits, and said collecting of said output light from each said selected tooth in said first and subsequent visits occurs at the same area of each respective tooth.

17. A method of determining the viability of teeth in a patient's mouth, comprising inserting a mouth part of a first means into the patient's mouth for illuminating at least successively each selected tooth with input light of at least two separated wavelengths, and determining by determining means including at least a respective part of said first means a number corresponding to a ratio of output light of said two wavelengths scattered from within each said tooth and originating as said input light, wherein said two wavelengths are selected to discriminate by their relative intensities in said output light the amount of hemoglobin in each said tooth and to optimize a signal-to-noise characteristic for said ratio.

18. The method of claim 17, said first wavelength being at 575 nm and said second wavelength being in the infrared.

19. The method of claim 17, said first wavelength being at 575 nm and said second wavelength being in the near infrared.

20. The method of claim 17, said first wavelength being at 575 nm and said second wavelength being in the range from 580 to 800 nm.

21. The method of claim 20, said range for said second wavelength being from 600 to 750 nm, whereby a higher signal to noise ratio is achieved in the determining of said ratio.

22. The method of claim 20, said second wavelength being at 585 nm.

23. The method of claim 20, said second wavelength being at 595 nm.

24. The method of claim 20, said second wavelength being in the vicinity of 655 nm.

25. The method of claim 20, said second wavelength being in the vicinity of 795 nm.

26. The method of claim 20, said second wavelength being in the vicinity of 655 nm.

27. The method of claim 20, said second wavelength being in the vicinity of 795 nm.

28. The method of claim 17, said first wavelength being at 585 nm and said second wavelength being at 595 nm.

29. A device for assessing the viability of a patient's teeth, comprising first means with a mouth part for being inserted into the mouth of the patient, for introducing into each selected tooth light of at least two different wavelengths and for receiving respective output light of said at least two different wavelengths scattered from within the respective selected tooth, while substantially excluding from the received output light any light originating with said input light and not being received from within the selected tooth, and for providing a respective signal for said output light of each of said at least two different wavelengths, and means for determining from said at least two respective signals a value indicating the relative amounts of the received output light at said two different wavelengths.

30. The device of claim 29 said mouth part of said first means including a light supply part and a light receiving part operatively connected to each other so as to be locatable as unit on respective opposite sides of each said selected tooth, said light supply part providing said introducing of said light to the selected tooth, and said light receiving part providing said receiving of said output light from the selected tooth.

31. The device of claim 29, said mouth part of said first means including a light supply part and a light receiving part operatively connected to be locatable as a unit on the same side of each said selected tooth, said light supply part providing said introducing of said light to the selected tooth, and said light receiving part providing said receiving of said output light from the selected tooth.

32. The device of claim 29, said first wavelength being at 575 nm and said second wavelength being in the infrared.

33. The device of claim 29, said first wavelength being at 575 nm and said second wavelength being in the near infrared.

34. The device of claim 29, said first wavelength being at 575 nm and said second wavelength being in the range from 580 to 800 nm.

35. The device of claim 34, said range for said second wavelength being from 600 to 70 nm, whereby a higher signal to noise ratio is achieved in the determining of said ratio.

36. The device of claim 34, said second wavelength being at 585 nm.

37. The device of claim 34, said second wavelength being at 595 nm.

38. The device of claim 34, said second wavelength being in the vicinity of 655 nm.

39. The device of claim 34, said second wavelength being in the vicinity of 795 nm.

40. The device of claim 34, said second wavelength being in the vicinity of 655 nm.

41. The device of claim 34, said second wavelength being in the vicinity of 795 nm.

42. The device of claim 29, said first wavelength being at 585 nm and said second wavelength being at 595 nm.

* * * * *